(12) United States Patent
Murata

(10) Patent No.: US 8,349,005 B2
(45) Date of Patent: Jan. 8, 2013

(54) METHOD FOR BURYING IMPLANT TO CHOROID

(76) Inventor: Masatoshi Murata, Morioka (JP)

( * ) Notice: Subject to any disclaimer, the term of this patent is extended or adjusted under 35 U.S.C. 154(b) by 151 days.

(21) Appl. No.: 12/929,112

(22) Filed: Jan. 3, 2011

(65) Prior Publication Data
US 2012/0172984 A1    Jul. 5, 2012

(51) Int. Cl.
*A61F 2/14*    (2006.01)
(52) U.S. Cl. ............................................... 623/4.1
(58) Field of Classification Search .......... 424/427–428; 623/4.1, 6.63; 128/898; 604/521
See application file for complete search history.

(56) References Cited

U.S. PATENT DOCUMENTS

| | | | |
|---|---|---|---|
| 5,869,079 A | 2/1999 | Wong et al. | |
| 6,397,849 B1 * | 6/2002 | Bowman et al. | 128/898 |
| 6,899,877 B2 * | 5/2005 | Peyman | 424/94.64 |
| 8,003,124 B2 * | 8/2011 | Varner et al. | 424/427 |

FOREIGN PATENT DOCUMENTS

| | | |
|---|---|---|
| WO | WO 96/38174 | 12/1996 |
| WO | WO 2004/062649 | 7/2004 |
| WO | WO 2004/066979 | 8/2004 |
| WO | WO 2004/066980 | 8/2004 |
| WO | WO 2005/107707 | 11/2005 |
| WO | WO 2005/107708 | 11/2005 |
| WO | WO 2005/107718 | 11/2005 |
| WO | WO 2005/107727 | 11/2005 |
| WO | WO 2005/110365 | 11/2005 |
| WO | WO 2005/110368 | 11/2005 |
| WO | WO 2005/110380 | 11/2005 |
| WO | WO 2005/110424 | 11/2005 |
| WO | WO 2005/112884 | 12/2005 |
| WO | WO 2006/093758 | 9/2006 |
| WO | WO 2006/105403 | 10/2006 |
| WO | WO 2006/110487 | 10/2006 |
| WO | WO 2006/122165 | 11/2006 |
| WO | WO 2006/127987 | 11/2006 |
| WO | WO 2007/084765 | 7/2007 |
| WO | WO 2007/092620 | 8/2007 |
| WO | WO 2007/121485 | 10/2007 |
| WO | WO 2008/079674 | 7/2008 |
| WO | WO 2008/129554 | 10/2008 |

\* cited by examiner

*Primary Examiner* — William H. Matthews
(74) *Attorney, Agent, or Firm* — Manabu Kanesaka

(57) ABSTRACT

After a vitreous gel of an eyeball is liquefied, a choroid is exposed; a vitreous humor is sucked to decrease a pressure in a vitreous body; a pocket is formed in the choroid; and then an implant is inserted into the pocket.

4 Claims, 6 Drawing Sheets

METHOD FOR BURYING IMPLANT TO CHOROID

BACKGROUND OF THE INVENTION

1. Field of the Invention

The present invention relates to a treatment method for eyes, and more particularly, to a method for burying an implant in the choroid.

2. Description of the Related Art

Many inflammatory diseases or proliferative diseases in a posterior segment of an eyeball, e.g., uveitis, diabetic retinopathy, proliferative vitreoretinopathy, macular degeneration, and others are serious disorders that require medication over a long period of time.

When carrying out systemic administration of medicines with respect to such a disorder, the administration of a large amount of medicines is required, and hence a systemic side-effect is concerned. Further, when carrying out instillation of ophthalmic drugs, a distance for the drug to reach a retina or a choroid lesion is long, there is a problem of an influence of tears or corneal permeability, and hence exercising an effective action is difficult.

Therefore, it is considered that administration of a medicine using a sustained release drug implant is suitable for a treatment of a posterior eye segment.

Here, as a sustained release system for a steroid, it has been reported that administration of dexamethasone or fluocinolone to a vitreous body is effective for a treatment of uveitis (Dexamethasone sustained drug delivery implant for the treatment of severe uveitis. Author: Jaffe G J, Pearson P A, Ashton P, Volume:20 Issue:4, Page:402-3 Year:2000 Source: Retina, Fluocinolone acetonide sustained drug delivery device to treat severe uveitis. Author: Jaffe G J, Ben-Nun J, Guo H, Dunn J P, Ashton P, Volume:107 Issue:11, Page:2024-33 Year:2000 Source: Ophthalmology). These sustained release drugs have compositions similar to that of an antiviral drug, but an antiviral drug implant may cause serious complications such as intravitreous hemorrhage, retinal detachment, intraocular inflammation, and others in some cases, and hence actually using such an implant for treatments is still difficult.

Further, it has been recently reported that sustained release from a sclera triggers an effective action of a drug to the posterior eye segment, and it has been informed that sustained release of a betamethasone phosphate from the sclera effectively acts on a vitreous body, a retina, or a choroid (Biodegradable intrascleralimplant for sustained intraocular delivery of betamethasone phosphate. Author: Okabe J, Kimura H, Kunou N, Okabe K, Kato A, Ogura Y, Volume:44 Issue:2, Page:740-4 Year:2003 Source: Invest Ophthalmol Vis Sci, Intraocular tissue distribution of betamethasone after intrascleral administration using a non-biodegradable sustained drug delivery device. Author: Okabe K, Kimura H, Okabe J, Kato A, Kunou N, Ogura Y, Volume:44 Issue:6, Page:2702-7 Year:2003 Source: Invest Ophthalmol Vis Sci).

However, since a distance between the sclera and the retina is too long to impregnate with a drug, providing a sufficient medicinal effect to the retina or the vitreous body on the inner side thereof is relatively difficult.

On the other hand, to exert an action of the drug to the retina or the vitreous body, it is considered that effecting sustained release of the drug from the choroid that is immediately adjacent to the retina is further effective. If the sustained release of the drug is performed from the choroid, an amount of the drug can be reduced, which is advantageous in terms of side-effects. Therefore, enabling implanting the betamethasone phosphate into the choroid is considered to be more preferable.

Here, as literatures concerning such a technology, there are a booklet of International Publication No. 2006/093758 and U.S. Pat. No. 5,869,079. These literatures describe burying an implant into the choroid.

However, an operation of burying an implant into the choroid is not easy. Although the choroid is a tissue placed between the sclera and the retina, the retina is an important tissue including a photoreceptor cell, a bipolar cell, a ganglion cell, a Müller cell, and others, and hence the closest attention must be paid in the operation for the choroid to avoid damages to the retina.

However, since the choroid is generally a thin membrane having a thickness of approximately 0.3 mm in case of a human and tensile force functions on the outer side due to an ocular pressure, an operation of forming a pocket utilized to insert an implant into the choroid without damaging the retina is very difficult, and a technology that facilitates this operation has not been found yet.

SUMMARY OF THE INVENTION

Thus, the present inventor has keenly conducted studies and developed an operative method of easily burying an implant into the choroid.

That is, it is an object of the present invention to provide an operative method of liquefying a vitreous gel of an eyeball, then exposing a choroid, subsequently sucking a vitreous humor to reduce a pressure in the vitreous body, incising the choroid in a tangential direction, distending the choroid by bleeding to make a space, and forming a pocket in the choroid, thereby easily burying an implant into the choroid.

To achieve this object, according to the present invention, there is provided a burying method of an implant into a choroid, comprising: liquefying a vitreous gel in an eyeball; exposing the choroid; sucking a vitreous humor to decrease an internal pressure of a vitreous body; forming a pocket in the choroid; and inserting the implant into the pocket.

Further, according to the burying method of the implant into the choroid of the present invention, it is preferable that the formation of the pocket in the choroid is accomplished by stabbing an incision instrument into the choroid obliquely with respect to a surface of the choroid; moving this instrument to a position where bleeding occurs; and then, after the distension of the choroid by the bleeding, moving the incision instrument in the choroid in parallel to the layer of the choroid, to incise the choroid.

DESCRIPTION OF THE PREFERRED EMBODIMENT

An embodiment of a burying method of an implant into a choroid according to the present invention will now be described hereinafter in detail with reference to the accompanying drawings. First, a configuration of an eye will be explained with reference to FIG. 1 and FIG. 2.

[Configuration of Eye]

Figure 1:
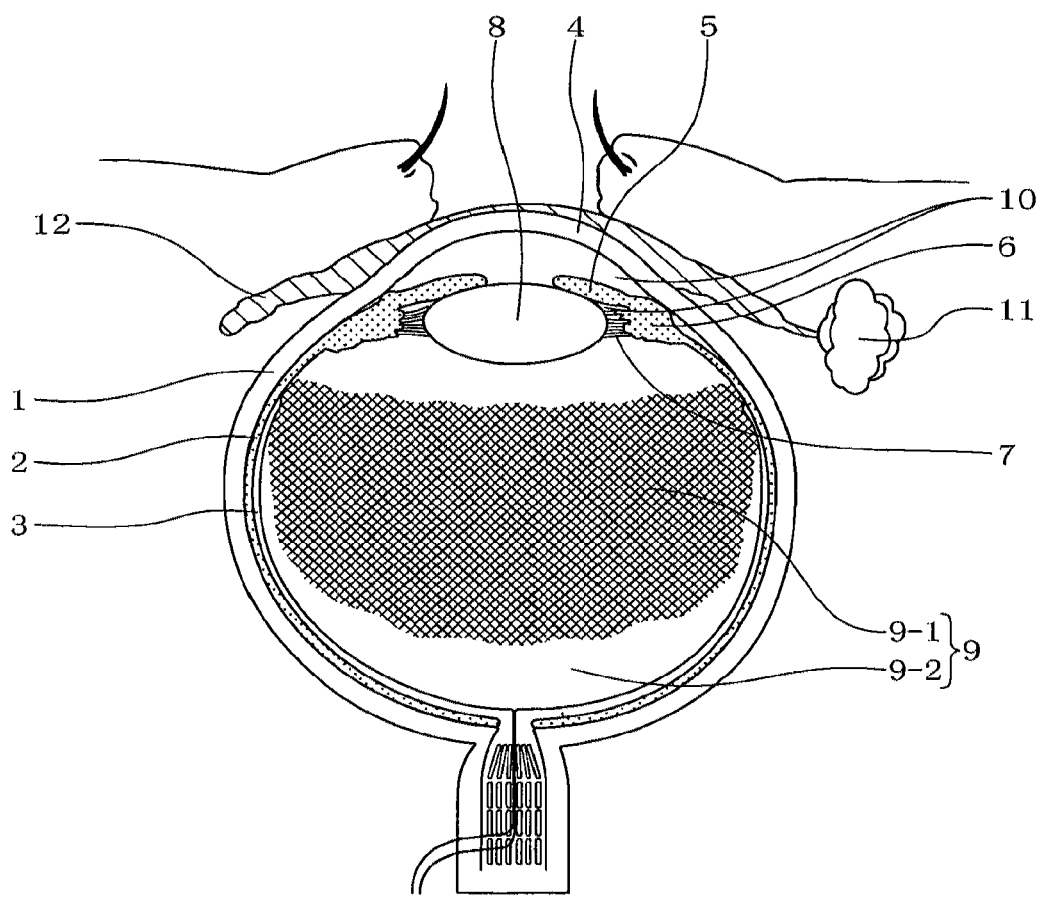
FIG. 1 is a view showing a configuration of an eyeball.
Figure 2:
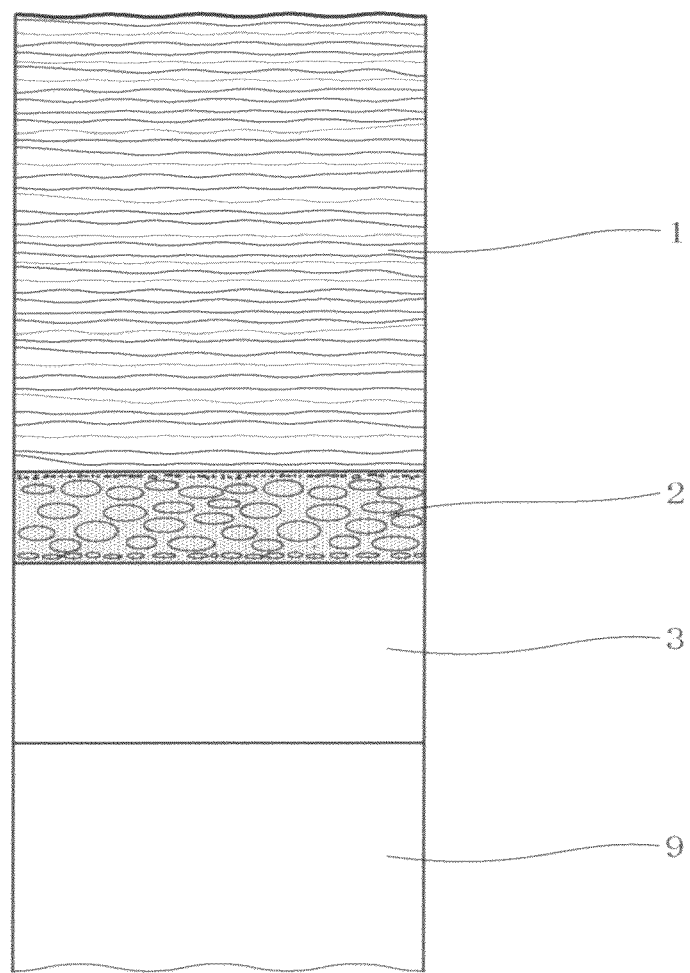
FIG. 2 is a view showing a configuration of three layers in the eyeball.

An eye consists of an eyeball, an ocular adnexa, and an optic nerve. As shown in FIG. 1, the eyeball consists of parts constituting an outer wall such as a sclera 1, a choroid 2, a retina 3, a cornea 4, an iris 5, a ciliary body 6, a Zinn zonule 7, and others and parts constituting contents such as a crystalline lens 8, a vitreous body 9, an aqueous humor 10, and others. The inside of vitreous body 9 is divided into a vitreous gel 9-1 and a liquefied vitreous body 9-2. In case of a human, the liquefied vitreous body 9-2 is observed when reaching manhood, and the vitreous gel 9-1 is decreased but the liquefied vitreous body 9-2 is increased with advancing age. Furthermore, the ocular adnexa consists of a lacrymal apparatus 11, a conjunctiva 12, and others. An outer wall of a posterior eye segment has a three-layer configuration in which an outer layer is the sclera 1, an intermediate layer is the choroid 2, and an inner layer is the retina 3. FIG. 2 shows a layer configuration of this posterior eye segment.

It is to be noted that FIG. 1 shows the configuration of a human eye, but the present invention does not restrict a target for burying an implant into the choroid 2 to a human, and the invention can be applied to various animals having the same augen structure as that of a human, e.g., a rabbit, a monkey, a cat, a horse, a cow, and others.

The sclera 1 is an opalescent hard layer, and its front side is connected to the cornea. The sclera 1 hardly allows light to permeate therethrough and has a function of preventing unnecessary light from entering into the eyeball and protecting the inside of the eyeball. A thickness of the sclera 1 is approximately 1.0 mm to 1.5 mm in a posterior wall of the eyeball, and it is approximately 0.25 to 0.3 mm at the thinnest part having an ocular muscle attached thereto.

The choroid 2 is a thin blackish layer sandwiched between the outer sclera 1 and the inner retina 3. Many blood vessels are present in the choroid 2, thereby supplying nourishment to an outer layer of the retina having no blood vessel. A thickness of the choroid 2 is approximately 0.2 to 0.3 mm.

The retina 3 is a thin membrane consisting of 10 layers, and it has a thickness of 0.3 mm to 0.4 mm at a central part and a thickness of approximately 0.15 mm at a peripheral part. In the retina 3, two types of photoreceptor cells called a rod and a cone are present. Besides, in the retina 3, important cells such as a ganglion cell or a Müller cell or many blood vessels are present. A macular region having many cones is present at the center of a rear part of the retina 3. This macular region is a part having the sharpest vision in the eyeball.

The vitreous body 9 is a clear and colorless gel filling the inside of the eyeball, and 99% of this vitreous body 9 is water. The vitreous body 9 is in contact with the rear side of the crystalline lens and partially attached to the retina 3 on the inner side of the eyeball, but a major part of the vitreous body 9 is lightly in contact with the retina 3.

Here, as one of diseases in the macular region of the retina 3, there is macular degeneration. The macular region has the much better visual performance than other regions of the retina 3, and it plays an important role to maintain visual function.

In the macular degeneration, bleeding or exudates occurs in the macular degeneration, whereby a symptom such as a decrease in vision or metamorphopsia occurs. There is macular degeneration which is of a type that occurs when an abnormal blood vessel called a new blood vessel which is not present in a healthy state is generated from the choroid 2 and it grows toward the retina 3 side. A wall of this new blood vessel is very fragile, and bleeding or exudate occurs in the macular region.

A Bruch membrane is present between the choroid 2 and the retina 3, and a decrease in vision does not occur when the new blood vessel is present under the Bruch membrane. However, when the new blood vessel bursts through the Bruch membrane into a region under or above a retinal pigment epithelium, growth is precipitously facilitated, exudation of blood becomes intensive, and vision is considerably decreased. In particular, when the new blood vessel has reached a central fovea, since conducting a laser photocoagulation results in an extreme decrease in vision, this operative method cannot be utilized, and an effective treatment is difficult.

As a method of performing medication with respect to such a disease in the choroid 2 or the retina 3, there is a method of burying an implant that effects sustained release of a drug in the sclera 1, as mentioned above.

Here, as compared with inserting an implant into the sclera 1, inserting an implant into the choroid 2 is considered to be preferable since a distance from the implant to an affected area is reduced, a high treatment effect can be obtained, and an amount of medication can be decreased.

However, as compared with a burying operation of an implant into the sclera 1, a burying operation of an implant into the choroid 2 is very difficult, and conducting this operation has not been reported yet.

That is, since the sclera 1 is a hard and thick layer constituting the outer layer, a pocket required to insert the implant can be relatively easily formed. On the other hand, the choroid 2 is a thin membrane placed on the inner side of the sclera 1, and the retina 3 that is very thin and fulfills the most important function for visual acuity is present on the immediately inner-side of the choroid 2. Therefore, an operation of forming a pocket used for inserting the implant into the choroid 2 has a high risk of damaging the retina 3, and a regular method that is utilized when forming a pocket in the sclera 1 is very dangerous.

Thus, the burying method of an implant into the choroid according to the present invention can reduce the risk of damaging the retina 3 when forming the pocket in the choroid 2 as will be described later.

[Burying Method of Implant into Choroid]

Figure 3:
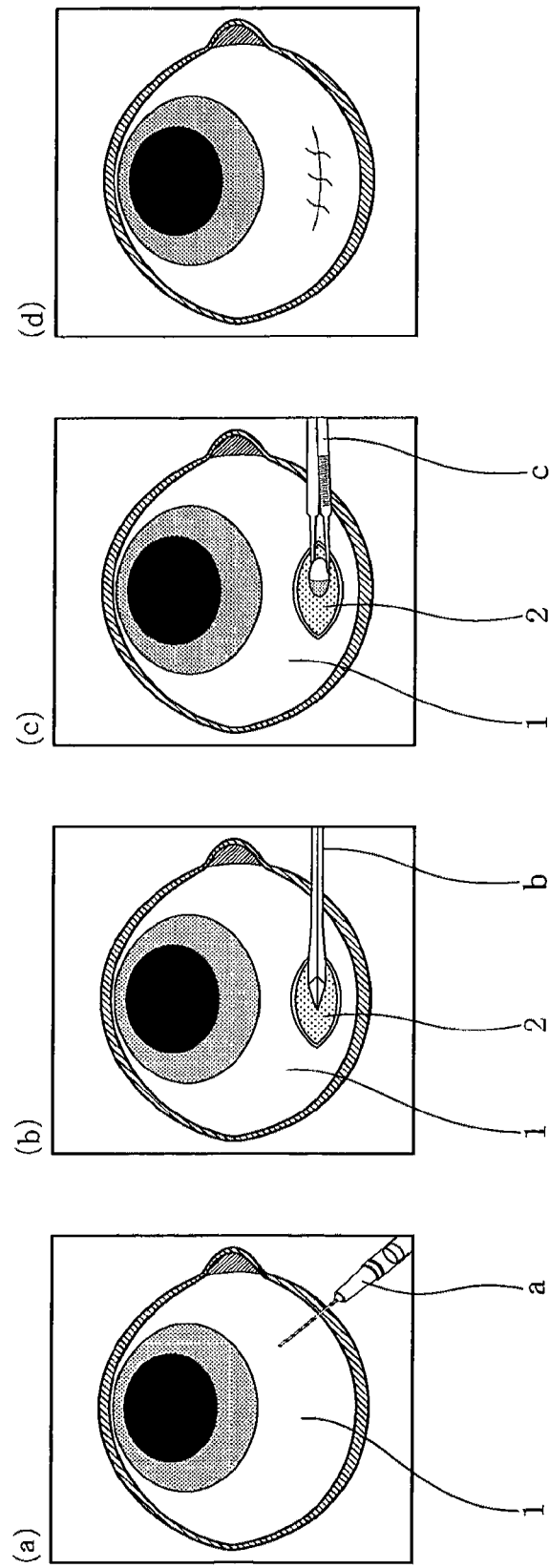
FIG. 3 is views showing an outline of a burying method of an implant into a choroid according to an embodiment of the present invention.
Figure 4:
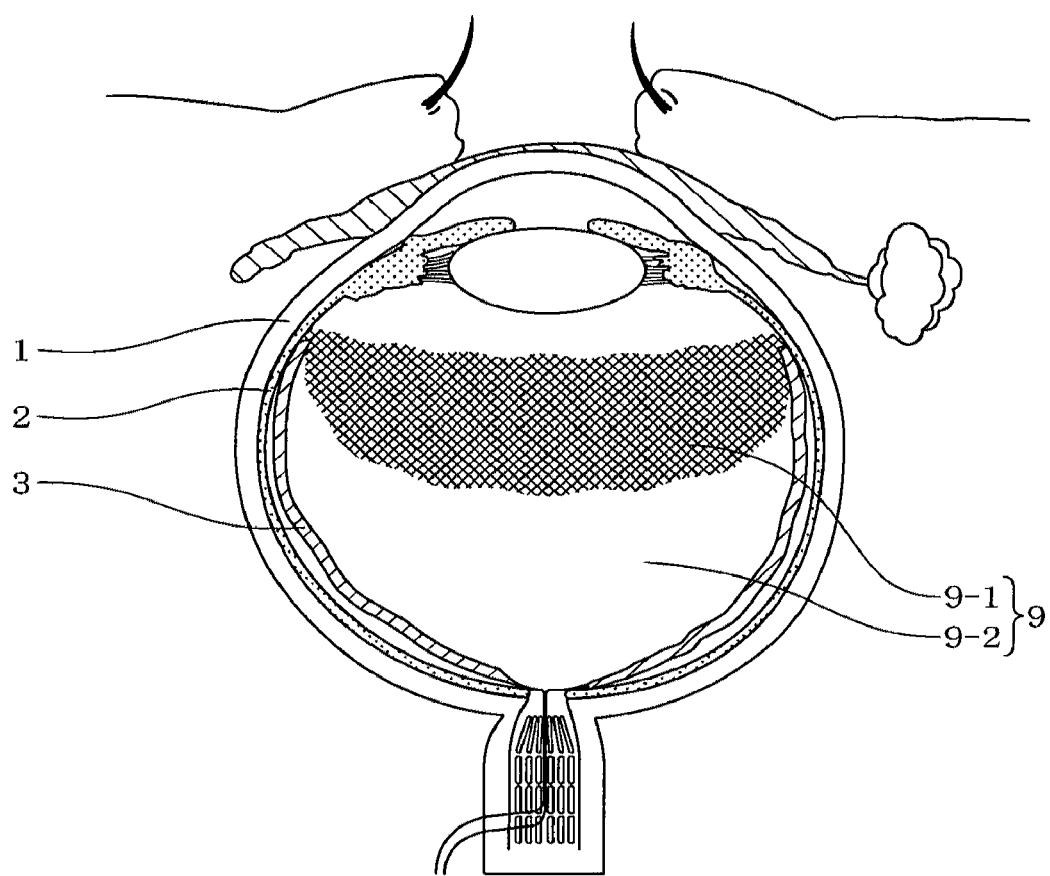
FIG. 4 is a view showing a state of the eye after sucking a vitreous humor in the burying method of an implant into a choroid according to the embodiment of the present invention.
Figure 5:
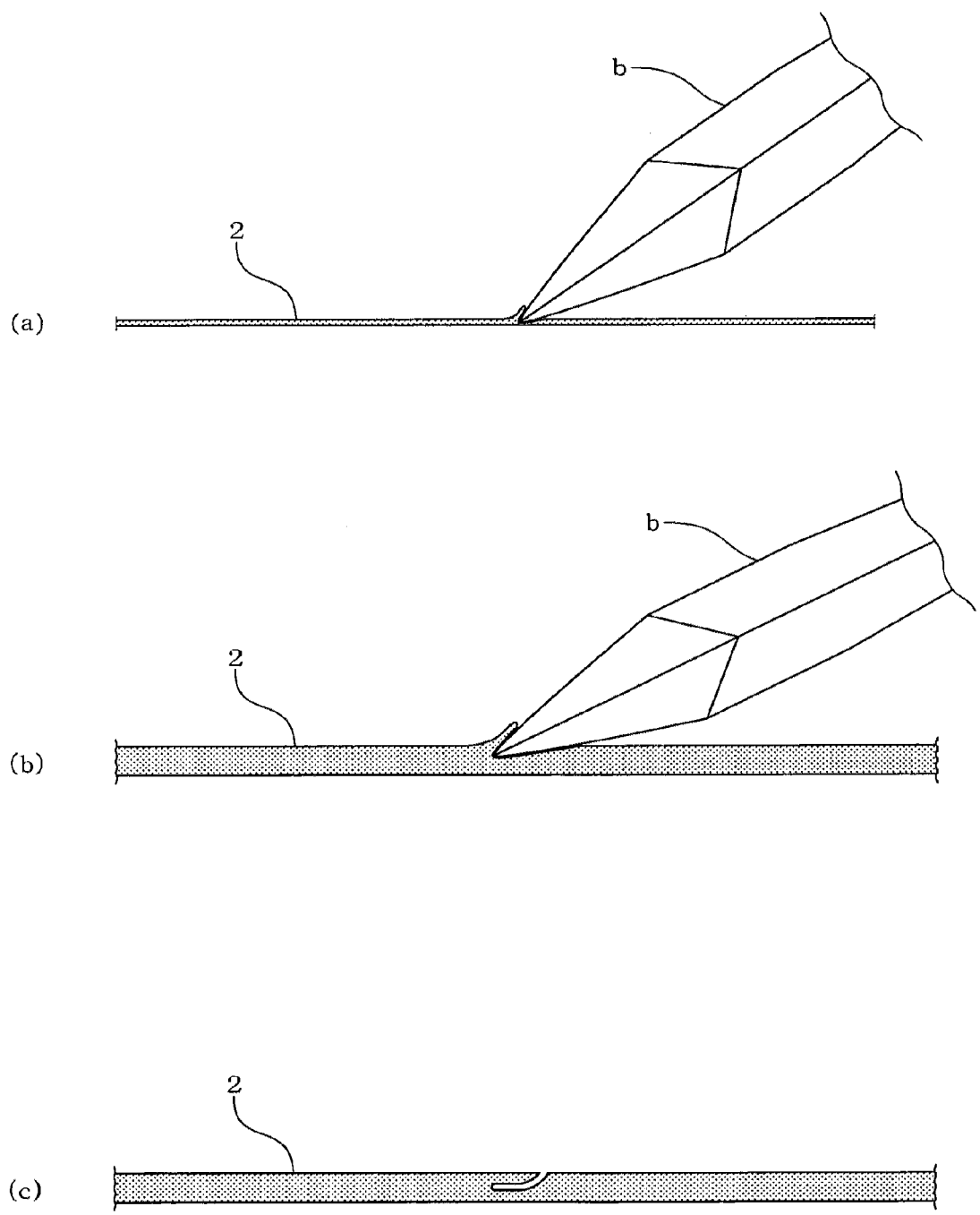
FIG. 5 is views showing incision of the choroid, distension of the choroid, and formation of a pocket in the choroid in the embodiment according to the present invention.
Figure 6:
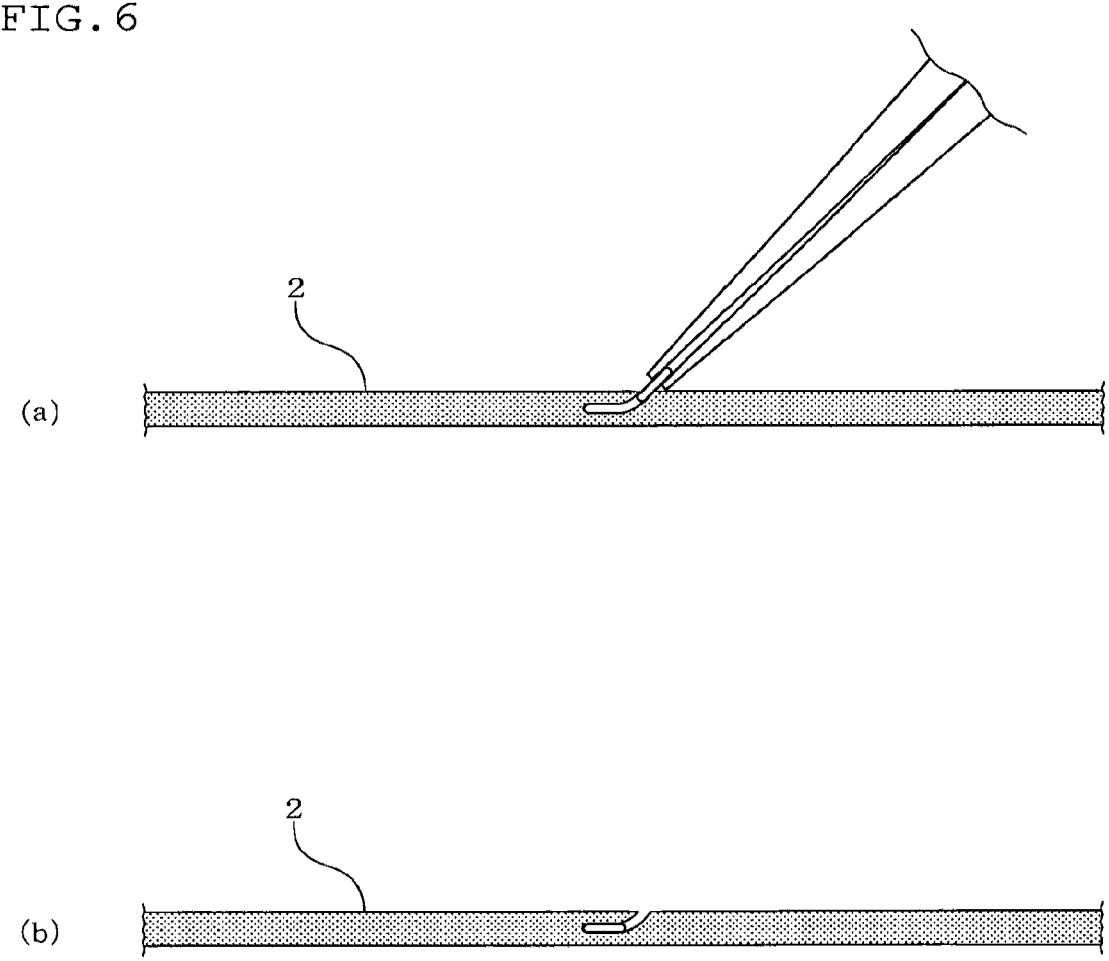
FIG. 6 is a view showing insertion of an implant into the choroid in the embodiment according to the present invention.

The burying method of an implant into a choroid according to the present invention will now be described with reference to FIG. 3 to FIG. 6. FIG. 3 show an outline of the burying method of an implant into a choroid according to this embodiment, and FIG. 4 to FIG. 6 show detailed contents of steps in the burying method of an implant into a choroid according to this embodiment. It is to be noted that a rabbit is used as a target of burying an implant into its choroid in the following embodiment and examples, but the present invention can be applied to humans. Further, the present invention is satisfactory as long as a vitreous gel of an eyeball can be liquefied and a choroid can be exposed, then a vitreous humor can be sucked to reduce a pressure in the vitreous body, a pocket can be subsequently formed in the choroid, and an implant can be inserted into the pocket, and the present invention is not restricted to specific matters described in the following embodiment and examples.

(A) Step of Liquefying Vitreous Gel

First, the vitreous gel in the eyeball of the target animal is liquefied. In this embodiment, an example where a white domestic rabbit is used as the target animal will be explained. The white domestic rabbit can be easily obtained, has eyeballs each having a constitution similar to that of a human eyeball, and can be used as a model animal with an ocular disease, which is preferable.

The vitreous body consists of a membrane and jelly-like contents enveloped by this membrane. A liquefacient is injected into this vitreous body to liquefy the vitreous gel. A proteolytic enzyme can be used as the liquefacient, whereby proteins constituting the vitreous gel can be broken up to carry out liquefaction. It is to be noted that, in case of a human, the vitreous gel has been already partially liquefied at maturity, but this liquefacient can further promote liquefaction, and the vitreous body can be softened by sucking and removing the vitreous humor.

For example, a general anesthesia and an ophthalmic anesthesia are given to a three-month-old white domestic rabbit, and then a vitreous surgical lens is placed on a cornea. Furthermore, a syringe needle a is inserted from a pars plana as shown in FIG. 3(a) while observing an ocular fundus with the aid of a microscope, and, e.g., 100 μL (a concentration of 150 IU/mL) of hyaluronidase is injected into the vitreous body. At this time, after approximately 100 μL of the vitreous humor is taken out or put in above an optic disc for approximately 10 times, sucking and removing approximately 50 μL of the vitreous humor is preferable.

As a result, an internal pressure of the vitreous body is increased by the injection of hyaluronidase, but carrying out the suction in this manner enables reducing the internal pressure of the vitreous body. The vitreous humor must be sucked at a later-described step of sucking the vitreous humor, but the vitreous humor does not have to be sucked at this step of liquefying the vitreous gel. Furthermore, a liquefacient is not restricted in particular.

Moreover, such white domestic rabbits are reared for one to seven days. As a result, hyaluronan constituting the vitreous gel is degraded, thereby liquefying the vitreous gel.

(B) Step of Exposing Choroid

After elapse of one to seven days, a general anesthesia and an ophthalmic anesthesia are again given to each of these white domestic rabbits, then a conjunctiva on the lower side is incised with the aid of a microscope, and the sclera 1 which is approximately 6 mm apart from a corneal limbus region is subsequently incised as shown in FIG. 3(b) to expose the choroid 2. The incision can be performed by using an incision instrument b such as a surgical knife.

(C) Step of Sucking Vitreous Humor

Moreover, the vitreous surgical lens is placed on the cornea, the syringe needle is inserted from the pars plana while observing the ocular fundus with the aid of a microscope, and approximately 200 μl of the vitreous humor is sucked immediately above the optic disc. As a result, the internal pressure of the vitreous body 9 can be reduced to obtain a soft state as depicted in FIG. 4. This drawing shows a state that the retina is detached thinly from the choroid. Consequently, perforation can hardly occur in the retina 3 when incising the choroid 2, thus reducing a possibility of damaging the retina 3.

(D) Step of Forming Pocket

Then, in the choroid 2, a pocket used for burying an implant is formed. At this time, as shown in FIG. 5(a), the incision instrument b is slightly inclined with respect to the exposed choroid 2 in a tangential direction, and the choroid is shallowly incised by using this instrument.

Here, a layer including many blood vessels is present in the choroid 2, and bleeding occurs when the end of the incision instrument b reaches this blood vessel layer. Therefore, the knife is stopped at a position where the bleeding has occurred until approximately a period of 0.5 minute to 2 minutes passes in this state, thereby largely distending the choroid 2 as shown in FIG. 5(b).

After a fixed time passes from the insertion of the incision instrument b into the choroid 2 and the choroid 2 is thereby distended, the incision instrument b is moved in the choroid 2 in parallel to the layer of the choroid 2 (in the tangential direction) to perform incision, whereby a pocket is formed in the choroid 2 as depicted in FIG. 5(c).

At this time, it is preferable to move the incision instrument b at a position corresponding to a half of a thickness of the layer of the choroid 2 in parallel to the layer of the choroid 2 (in the tangential direction) to carry out the incision. It is to be noted that the incision instrument b does not have to be maintained in the choroid 2 as it is during the fixed period after the insertion of the incision instrument b into the choroid 2, and the incision instrument b may be taken out.

As described above, according to the burying method of an implant into a choroid of this embodiment, formation of the pocket can be facilitated by forming the pocket after distending the choroid 2 which is fundamentally thin, and the possibility of damaging the retina 3 can be reduced.

It is to be noted that the phrase "after distending" does not mean a time point after full completion of the distension alone, and it includes, for example, a time point at which the choroid 2 is distended to a fixed thickness or above, e.g., twofold to fivefold, i.e., a time paint in the distension.

When forming the pocket in the choroid 2, the incision instrument b such as a surgical knife or a spatula is inserted into an incised part of the choroid 2, and the pocket (a pocket-like space) is formed at a position corresponding to a half of the thickness of the layer of choroid 2.

It is preferable for the pocket to have a size that enables insertion of a pellet having, e.g., a diameter of 1 mm and a thickness of approximately 0.2 mm as an implant. Therefore, it is preferable to use the incision instrument to form a square or rectangular incision having each side of approximately 1 m to 2 mm in parallel to the layer of the choroid 2. Moreover, a strong hemostatic agent such as Bosmin is utilized to stop bleeding.

It is to be noted that a shape of the implant does not have to be a columnar shape, and a horizontal cross section of the implant may have an elliptic shape or a rectangular shape and so on. Additionally, since a size of the implant greatly differs depending on a type of an implant burying target living matter or a size of an individual, it is not restricted. For example, a pellet that is 0.1 to 2 mm long and 0.1 to 2 mm wide and has a thickness of approximately 0.05 to 0.5 mm can be used as the implant.

(E) Step of Burying Implant

Subsequently, as shown in FIG. 3(c) and FIGS. 6(a) and (b), a forceps c is utilized to bury the implant in the pocket.

As the implant, an adequate one can be appropriately selected in accordance with a disease. For example, an implant containing a medicine such as betamethasone can be created and used. The betamethasone is an adrenal cortical steroid drug that controls inflammation or an allergic action.

(F) Step of Suture

Finally, as shown in FIG. 3(d), the sclera 1 and the conjunctiva are sequentially sutured, and an ophthalmic ointment is put into the eye to terminate the operation.

As described above, according to the burying method of an implant into choroid according to this embodiment, when burying the implant into the choroid, the vitreous gel is first liquefied, and then the vitreous humor is sucked, thereby softening the eyeball. Further, the pocket can be formed after increasing a thickness of the choroid.

Therefore, when forming the pocket in the choroid, the possibility of damaging the retina can be reduced, and the implant can be safely buried in the choroid.

EXAMPLE

An example of the burying method of an implant into a choroid according to the present invention will now be described.

Example 1

[Creation of Implant]

100 mg of a polylactate (manufactured by Wako Pure Chemical Industries, Ltd.) and 100 mg of a betamethasone phosphate (manufactured by Sigma-Aldrich Corporation) were dissolved in 5 ml of an acetic acid, and this substance was freeze-dried at −80° C. for 48 hours. Then, an obtained composition was pressed to create a pellet having a diameter of 1 mm and a thickness of 0.2 mm, and this pellet was determined as an implant to be buried in a choroid.

[Burying Method of Implant into Choroid]

(A) Step of Liquefying Vitreous Gel

As an implant burying target animal, four three-month-old Japanese white domestic rabbits (bred by Japan SLC, Inc, each having a weight of 2 to 2.5 kg) were used, and the implant was buried into a choroid of each rabbit based on the following method.

Ketamine (5 mg/kg) and xylazine (2 mg/kg) were utilized for a general anesthesia given to the Japanese white domestic rabbits, and 2%-xylocalne was used for an ophthalmic anesthesia. These anesthesia were given by general methods, respectively.

Subsequently, for the purpose of liquefying the vitreous body, hyaluronidase (manufactured by Wako Pure Chemical Industries, Ltd.) was injected into the vitreous body one week before burying the implant.

Concretely, a vitreous surgical lens (manufactured by Handaya Co., Ltd., HE196) was placed on a cornea, and a needle of 27 G and a syringe of 1 cc (manufactured by Terumo Corporation) were utilized to inject 100 μL (150 IU/mL) of the hyaluronidase into the vitreous body from a pars plana with the aid of a microscope (manufactured by Topcon Corporation, OMS600) while observing an ocular fundus.

Subsequently, pipetting was carried out for approximately 10 times immediately above an optic disc, and then 50 μL of the vitreous humor was sucked.

(B) Step of Sucking Vitreous Humor

After one week, a 15-degree knife (manufactured by Mani Inc.) was utilized to incise a conjunctiva on the lower side with the aid of a microscope, and then a sclera was incised at a position that is 6 mm below a corneal limbus portion to expose the choroid.

Subsequently, a vitreous operative lens was again placed on the cornea, a needle of 27 G and a syringe of 1 cc were inserted from the pars plana, and approximately 200 μL of the vitreous humor was sucked immediately above the optic disc while observing the ocular fundus by using a microscope.

(C) Step of Burying Implant Subsequently, MVR of 25 G (manufactured by Mani Inc.) was utilized, and its end was slightly inclined toward the choroid side in a tangential direction of a surface of the choroid, shallowly incised into the choroid, and stopped at a position where bleeding occurred.

After elapse of a few minutes, the MVR was moved ahead in parallel to the surface of the choroid at a position corresponding to a half of the thickness of the choroid layer, and the choroid was incised approximately 1 mm. Then, a spatula was inserted into an incised part of the choroid, moved ahead in parallel to the surface of the choroid at the position corresponding to the half of the thickness of the choroid layer, and also moved in left and right directions, thereby forming a pocket consisting of an incision of approximately 2 mm×2 mm. At this time, MQA (manufactured by Inami & Co., Ltd.) impregnated with Bosmin was utilized to stop bleeding.

The pellet was buried in this pocket by using a forceps (manufactured by Inami & Co., Ltd., M-1R).

Finally, the sclera was sutured by using 9-0 nylon (manufactured by Mani Inc.), then the conjunctiva was sutured by using 6-0 silk (manufactured by Mani Inc.), and an ofloxacin ophthalmic ointment (manufactured by Santen Pharmaceutical Co., Ltd.) as an antibiotic was put in the eye to terminate the operation.

[Evaluation of Concentration of Betamethasone Phosphate after Burying Implant]

After four weeks from a day the implant burying treatment was given, a concentration of the betamethasone phosphate in the choroid of each of the four Japanese white domestic rabbits used in Example 1 was measured by a high-performance liquid chromatography (HPLC). Concretely, the eyeball was enucleated from each of the Japanese white domestic rabbits, and the choroid was taken out from this eyeball. Three ml of a hydrochloric acid of 0.2 M was added to this choroid, and the choroid was washed and then centrifugalized to obtain a supernatant. Thereafter, 3 ml of an acetic acid was added, and betamethasone was extracted. The acetic acid containing the betamethasone was dried and dissolved in 100 μl of a mobile phase, thereby creating an analytical sample.

Additionally, a C-18 reverse-phase column (150×6 mm; Shim-pack CLC-ODS; Shimadzu Corporation) was adopted, and methanol and 50 mM of a potassium dihydrophosphate aqueous solution (55:45) were used as an eluting solution. Ten μl of the sample was injected to it, and elution was effected at 40° C. and a flow velocity of 1.2 mL/minute. Further, an obtained eluate was analyzed in a wavelength of 240 nmm by using an absorptiometric detector (L-4200, manufactured by Hitachi Ltd.) to measure a concentration of the betamethasone in the choroid.

As a result, the concentration of the betamethasone phosphate in the choroid was 15.3±7.49 μg/ml (the number of samples: four eyes, mean±SD).

As described above, as the concentration of the betamethasone phosphate in the choroid subjected to sustained release from the implant buried by the burying method of an implant into a choroid according to the present invention, the effective concentration was maintained even after four weeks from burying.

Example 2

An implant consisting of a pellet containing the betamethasone phosphate was created by the same method as Example 1.

As a target animal for burying an implant into a choroid, two three-month-old Dutch rabbits (bred by Kitayama Labes Co., Ltd., each having a weight of 1.5 to 2 kg) were used, and an implant was buried into a choroid of each of these rabbits by the burying method of an implant into a choroid according to the present invention like Example 1.

[Ophthalmologic Evaluation of Eye State after Burying Implant]

To evaluate a state of each eye after burying the implant into the choroid, fluorescein angiography was carried out with respect to the Dutch rabbits used in Example 2 after eight weeks from the day the implant burying treatment was performed, and obtained photographs were analyzed. Additionally, a slit-lamp examination and a funduscopic examination were also conducted with respect to these Dutch rabbits.

As a result, perforation did not occur in the retina of each individual, and a obvious inflammation remark was not found in each implanted part of the choroid. Further, abnormality was not found in a cornea or an anterior chamber.

Therefore, it was revealed that the implant was safely inserted in the choroid by the burying method of an implant into a choroid according to the present invention.

[Histologic Evaluation]

Further, after eight weeks from the day the implant burying treatment was carried out, the eyeball was enucleated from each Dutch rabbit used in Example 2 and immersed in a mixture of 4%-glutaraldehyde and 2.5%-neutral buffered formalin liquid. Then, a test piece obtained by cutting the eyeball was dehydrated and immersed in paraffin to be solidified. Moreover, a microtome was utilized to obtain each flake, and this flake was dyed by using hematoxylin and eosin to be observed.

As a result, the implant was decomposed, and a part of the choroid where the implant was buried was substituted by a fibrous tissue. Further, the retina near the part where the implant was buried had a normal remark. It is to be noted that substitution of the fibrous tissue for the part where the implant was buried is a general phenomenon, and it is not a problem.

Based on the above-described results of the examples, according to the present invention, it was revealed that the possibility of damaging the retina when burying the implant into the choroid can be reduced and safety of the implant burying operation can be improved.

Furthermore, the concentration of the betamethasone phosphate in the choroid was maintained for at least four weeks as an effective concentration that can control inflammation without a serious tissue damage. Therefore, it was cleared that the implant into the choroid can be effectively used for a drug delivery system that effects sustained release of drugs in the eye.

According to the present invention, the gel in the membrane of the vitreous body can be liquefied to soften the eyeball. Therefore, it is possible to greatly reduce the possibility of damaging the retina when an incision instrument penetrates through the choroid at the time of inserting the incision instrument into the choroid after a decrease in ocular pressure.

Furthermore, the incision instrument is inserted into the choroid to cause bleeding and left at rest for a fixed time, a thickness of the choroid is increased, and a pocket is formed in this state, thereby easily forming the pocket in the choroid.

Moreover, since the implant is buried into the choroid in this manner, a treatment effect for a disease in a posterior eye segment region can be improved when inserting a drug as the implant.

Additionally, when a material that induces a disease, e.g., a composition containing a growth factor such as an FGF (a fibroblast growth factor) or a VEGF (a vascular endothelial growth factor) is inserted as the implant, a model animal affected with a specific disease such as macular degeneration can be produced.

According to such a method of the present invention, not only a model animal which is of a type that neovascularization is caused in a retina to decrease vision but also a model animal which is of a type that neovascularization is caused in a choroid alone can be produced, thereby creating a model animal closer to a human.

The present invention is not restricted to the foregoing embodiment or examples, and it is needless to say that various modifications can be carried out within the scope of the present invention.

For example, since the vitreous body is gradually liquefied with age, the step of liquefying the vitreous gel can be omitted if the vitreous body has been already liquefied. Moreover, a modification can be appropriately carried out. For example, a position in the sclera at which incision is performed or a position in the choroid at which the implant is inserted can be changed to a position different from those in the examples.

The present invention can be preferably utilized when burying an implant containing a medicine into a choroid of a human or a pet and effecting sustained release of the medicine in the eye for a long period of time to remedy, e.g., a disease in a retina or a vitreous body, or when burying an implant containing a fibroblast growth factor and others in a choroid of an experimental animal such as a rabbit and creating a model animal for use in clinical trials and others.

What is claimed is:

1. A burying method of an implant into a choroid, comprising:
    injecting a liquefacient into a vitreous body of an eyeball thereby liquefying a vitreous gel in the eyeball;
    exposing the choroid;
    sucking a vitreous humor to decrease an internal pressure of the vitreous body to reduce an ocular pressure thereby preventing an occurrence of perforation in a retina when forming a pocket in the choroid;
    inserting an incision instrument into the choroid obliquely with respect to a surface of the choroid, moving the incision instrument to a position where bleeding occurs, and after a distension of the choroid by the bleeding, moving the incision instrument in the choroid in parallel to a layer of the choroid, thereby forming the pocket in the choroid; and
    inserting the implant into the pocket.

2. The burying method of the implant into the choroid according to claim 1, wherein the liquefacient is hyaluronidase.

3. The burying method of the implant into the choroid according to claim 1, wherein, after elapse of 1 to 10 days from injection of the liquefacient into the vitreous body of the eyeball, a conjunctiva is incised, and then a sclera is incised to expose the choroid.

4. The burying method of the implant into the choroid according to claim 2, further comprising holding for 0.5 to 2 minutes after the bleeding occurs.

* * * * *